United States Patent
Tamper et al.

(10) Patent No.: US 11,040,950 B2
(45) Date of Patent: Jun. 22, 2021

(54) METHOD AND AN APPARATUS FOR RECOVERING FURFURAL

(71) Applicant: UPM-KYMMENE CORPORATION, Helsinki (FI)

(72) Inventors: Juha Tamper, Levänen (FI); Jere Salminen, Lappeenranta (FI); Mauno Miettinen, Lappeenranta (FI); Sami Turunen, Lappeenranta (FI); Meri Ventola, Lappeenranta (FI); Vilho Nissinen, Vehkataipale (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 16/473,790

(22) PCT Filed: Dec. 22, 2017

(86) PCT No.: PCT/FI2017/050930
§ 371 (c)(1),
(2) Date: Jun. 26, 2019

(87) PCT Pub. No.: WO2018/122454
PCT Pub. Date: Jul. 5, 2018

(65) Prior Publication Data
US 2020/0123121 A1   Apr. 23, 2020

(30) Foreign Application Priority Data
Dec. 30, 2016 (FI) .................. 20166049

(51) Int. Cl.
C07D 307/50 (2006.01)
(52) U.S. Cl.
CPC .................. C07D 307/50 (2013.01)
(58) Field of Classification Search
CPC .................................... C07D 307/50
See application file for complete search history.

(56) References Cited

U.S. PATENT DOCUMENTS

| | | | |
|---|---|---|---|
| 4,912,237 A | | 3/1990 | Zeitsch |
| 2012/0083611 A1* | | 4/2012 | Van Buijtenen ..... C07D 307/50 |
| | | | 549/489 |
| 2017/0233359 A1* | | 8/2017 | Marckmann ....... B01D 11/0223 |
| | | | 549/489 |

FOREIGN PATENT DOCUMENTS

| | | |
|---|---|---|
| DE | 740602 C | 11/1943 |
| EP | 2982703 A1 | 2/2016 |
| JP | 2013112661 A | 6/2013 |
| LV | 11950 B | 3/1998 |
| WO | 2006024242 A1 | 3/2006 |
| WO | 2010121367 A1 | 10/2010 |
| WO | 2012041990 A1 | 4/2012 |
| WO | 2016020269 A1 | 2/2016 |

OTHER PUBLICATIONS

Search Report from Finnish Patent Application No. 20166049 dated Sep. 6, 2017.
International Search Report from International Application No. PCT/FI2017/050930 dated Feb. 16, 2018.

* cited by examiner

*Primary Examiner* — Timothy R Rozof
(74) *Attorney, Agent, or Firm* — Nixon Peabody LLP

(57) ABSTRACT

In a method and an apparatus furfural is recovered from a steam stream (3) which is formed in a treatment of a pretreated wood based material (1). The pretreated wood based material (1) which comprises at least carbohydrates is treated in a steam treatment stage (2) in which the steam is released. The steam stream (3) which comprises furfural is supplied out from the steam treatment stage (2). A pretreated and steam-treated wood based material (4) which comprises carbohydrates is supplied out from the steam treatment stage (2), and the steam stream (3) is treated in a recovery stage (12*a*, 12*b*) for recovering a furfural based fraction (14*a*,14*b*).

21 Claims, 9 Drawing Sheets

METHOD AND AN APPARATUS FOR RECOVERING FURFURAL

CROSS-REFERENCE TO RELATED APPLICATIONS

This application is a U.S. National Stage of International Application No. PCT/FI2017/050930, filed Dec. 22, 2017, which claims the benefit of Finnish Patent Application No. 20166049, filed Dec. 30, 2016, both of which are hereby incorporated by reference in their entireties.

FIELD

The invention relates to a method and an apparatus for recovering furfural from a steam stream which is formed in a treatment of a pretreated wood based material.

BACKGROUND

It is known different methods for forming carbohydrates and lignin from different raw materials, such as biomass. Many bio-refinery processes, e.g. a hydrolysis, generate lignin and sugars after the treatment of the biomass. It is known that sugar streams comprise also other chemical compounds, e.g. furfural.

OBJECTIVE

The objective of the invention is to disclose a method for recovering furfural from wood based material. Another objective is to remove furfural from products and streams formed in the treatment of the wood based material. Another objective is to separate furfural from the wood based material.

SUMMARY

The method for recovering furfural is characterized by what is presented in claim 1.

The apparatus for recovering furfural is characterized by what is presented in claim 21.

BRIEF DESCRIPTION OF THE DRAWINGS

The accompanying drawings, which are included to provide a further understanding of the invention and constitutes a part of this specification, illustrate some embodiments of the invention and together with the description help to explain the principles of the invention. In the drawings.

DETAILED DESCRIPTION

Figure 1:
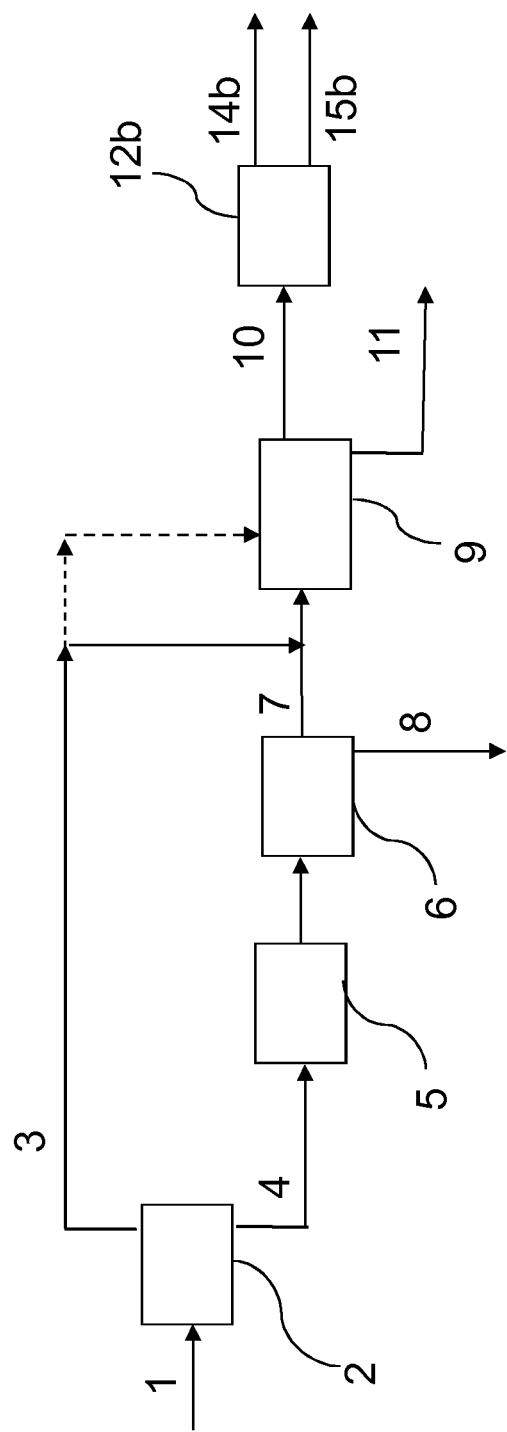
FIG. 1 is a flow chart illustration of a method according to one embodiment.

In a method for recovering furfural from a steam stream (3) which is formed in a treatment of a pretreated wood based material (1), the pretreated wood based material (1) which comprises at least carbohydrates is treated in a steam treatment stage (2) in which the steam is released, the steam stream (3) which comprises furfural is supplied out from the steam treatment stage (2), a pretreated and steam-treated wood based material (4) which comprises carbohydrates is supplied out from the steam treatment stage (2), and the steam stream (3) is treated in a recovery stage (12a, 12b) for recovering a furfural based fraction (14a,14b).

One embodiment of the method is shown in FIG. 1. Another embodiments of the method are shown in FIGS. 2-9.

The apparatus for recovering furfural comprises at least one a steam treatment stage (2) which comprises at least one steam treatment device and in which the pretreated wood based material (1) which comprises at least carbohydrates is treated and in which the steam is released, at least one discharge means, e.g. discharge device, for supplying the steam stream (3) which comprises furfural out from the steam treatment stage (2), at least one discharge means, e.g. discharge device, for supplying a pretreated and steam-treated wood based material (4) which comprises carbohydrates out from the steam treatment stage (2), and at least one recovery stage (12a, 12b) which comprises at least one recovery device, for recovering a furfural based fraction (14a,14b) from the steam stream (3).

In this context, a steam stream (3) means any steam stream which is formed, e.g. by separating, collecting or recovering, from a pretreated wood based material (1) in any steam treatment stage (2) and which comprises at least furfural. The steam stream (3) may comprise also organic acids, such as acetic acid or other organic acids. The steam stream may comprise also other components, such as side and degradation products. In one embodiment, the steam stream (3) is a steam fraction of the pretreated wood based material. The steam stream (3) may be formed from the pretreated wood based material after any suitable steam treatment stage, e.g. a steam explosion stage. The steam treatment stage comprises at least one steam treatment device, such as steam explosion device. In one embodiment, the steam treatment stage (2) is a steam explosion stage. In the steam explosion stage the pretreated wood based material (1) is treated by the steam explosion, in which hemicelluloses are treated and in which at least a part of polysaccharides of the hemicelluloses degrade into monosaccharides and oligosaccharides by means of a hydrolysis and in which pressure is rapidly released. In one embodiment, the steam treatment stage (2) comprises at least one separation step or separation device, e.g. cyclone, in which the steam stream (3) and the pretreated and steam-treated wood based material (4) are separated. Preferably, the steam stream (3) is in the form of steam or vapor, e.g. water based steam. In one embodiment, temperature of the steam stream is 90-110° C. after the steam treatment stage (2).

In one embodiment, the pretreated wood based material (1) comprises at least carbohydrates, such as C5 and/or C6 carbohydrates. In one embodiment, the pretreated wood based material (1) comprises at least C5 carbohydrates. In one embodiment, the pretreated wood based material (1)

comprises at least C5 and C6 carbohydrates. Further, in one embodiment, the pretreated wood based material comprises chemical compounds. In one embodiment, the pretreated wood based material comprises organic acids and/or other organic compounds. In one embodiment, the pretreated wood based material comprises furfural. Further, the pretreated wood based material (1) may comprise also other components, such as side and degradation products. In one embodiment, the pretreated wood based material (1) is formed from raw material. In one embodiment, the pretreated wood based material (1) is formed in a wood-to-sugar process. In one embodiment, the raw material comprises at least one of wood based material, wood, lignocellulosic biomass, agricultural residues, bagasse based material, sugarcane bagasse, corn based material, corn stover, wheat straw, rice straw, woody biomass, woody perennials, vascular plants, recycled brown board or deinking pulp, or their mixtures or their combinations. Preferably, the raw material is cellulose based material. The raw material may comprise lignin, lignocellulose, cellulose, hemicellulose, glucose, xylose and/or extractives. Further, the raw material may comprise other inherent structural components of biomass as well as foreign components such as enzymes or chemicals. In one embodiment, the raw material comprises wood based material or a mixture comprising wood based material. In one embodiment, the raw material is wood based material or a mixture comprising wood based material. In one embodiment, the wood based material is selected from hardwood, softwood or their combination. In one embodiment, the raw material comprises plant pieces, e.g. wood pieces. In one embodiment, the raw material comprises lignin, cellulose, carbohydrates and some chemical compounds. In one embodiment, the raw material may be treated by means of any suitable method for forming the pretreated wood based material (1). In one embodiment, the pretreated wood based material (1) is formed from the raw material which preferably is treated to dissolve at least a part of hemicellulose or a main part of hemicellulose. In one embodiment, the raw material is pre-treated, preferably by means of a suitable pretreatment stage which may be selected from the group comprising physical pretreatment, such as milling, extrusion, microwave pretreatment, ultrasound pretreatment and freeze pretreatment, chemical pretreatment, such as acid pretreatment, alkaline pretreatment, ionic liquid pretreatment, organosolv pretreatment and ozonolysis, physico-chemical pretreatment, such as steam explosion pretreatment, ammonia fiber explosion pretreatment, $CO_2$ explosion pretreatment, liquid hot water pretreatment and wet oxidation, biological pretreatment and their combinations. In one embodiment, the raw material is treated by the hydrolysis, e.g. acid hydrolysis, autohydrolysis, thermal hydrolysis, supercritical hydrolysis and/or subcritical hydrolysis, in which at least a part of hemicellulose is separated from the raw material in connection with the hydrolysis. In one embodiment, the raw material is treated by a dilute acid hydrolysis or an autohydrolysis. In one embodiment, the raw material is treated by the hydrolysis and by the steam explosion in one or more steps. In one embodiment, the raw material is treated by the catalytic pretreatment, e.g. by using acid or base as catalyst. In the pretreatment stage the raw material enters the reactor unit where the pretreatment takes place. The raw material can be treated by means of one or more pretreatment. The treated raw material can be then supplied directly, via an intermediate step, via an additional treatment step or via an intermediate storage as a pretreated wood based material (1) to a desired steam treatment stage (2). Further, in one embodiment, the raw material can be dewatered, e.g. by dewatering presses, and/or washed in one or two or more stages. The dewatering makes possible to separate sugar based streams.

In this context, a pretreated and steam-treated wood based material (4) means any stream which is formed, e.g. by separating, collecting or recovering, from a pretreated wood based material (1) in any steam treatment stage (2) and which comprises at least carbohydrates, such as C5 and/or C6 carbohydrates. In one embodiment, the pretreated and steam-treated wood based material (4) comprises at least C5 carbohydrates. In one embodiment, the pretreated and steam-treated wood based material (4) comprises at least C5 and C6 carbohydrates. Further, in one embodiment, the pretreated and steam-treated wood based material (4) comprises furfural and/or organic acids. Further, the pretreated and steam-treated wood based material (4) may comprise also other components, such as side and degradation products. In one embodiment, the pretreated and steam-treated wood based material (4) is a liquid fraction of the pretreated wood based material. Preferably, the pretreated and steam-treated wood based material (4) is formed from the pretreated wood based material after the same steam treatment stage, e.g. a steam explosion stage, than the steam stream (3). Preferably, the pretreated and steam-treated wood based material (4) is in the form of liquid, e.g. liquid or suspension.

In one embodiment, the pretreated and steam-treated wood based material (4) is diluted in a dilution stage (5) and is treated in a separation stage (6) in which C5 based fraction (7) and C6 based fraction (8) are separated. C5 based fraction (7) comprises at least C5 carbohydrates. C5 based fraction (7) may comprise furfural and/or organic acids. Further, C5 based fraction (7) may comprise also other agents or components.

In one embodiment, the pretreated and steam-treated wood based material (4) or C5 based fraction (7) is supplied to a concentration stage (9) for forming a concentrated carbohydrate based material (11) and the material stream (10) which comprises at least furfural. In one embodiment, temperature of the pretreated and steam-treated wood based material (4) or C5 based fraction (7) which is supplied to the concentration stage (9) is below 80° C., preferably below 75° C. The pretreated and steam-treated wood based material (4) or C5 based fraction (7) may be treated in one or more than one concentration stage (9). In one embodiment, the concentration stage (9) comprises at least two or more steps, and the material stream (10) is mainly discharged or recovered from the concentration stage after the first step. The material stream (10) may be in the form of steam or liquid after the concentration stage (9). In one embodiment, the material stream (10) is a vapor or a condensate of vapor from the concentration stage (9). In one embodiment, the material stream (10) is a top vapor of the concentration stage (9). Preferably, furfural accumulates into the material stream (10) during the concentration stage (9). In one embodiment, furfural accumulates mainly into the material stream (10) during the first concentration stage or during the first step of the concentration stage, and the material stream (10) comprising furfural is mainly collected during the first concentration stage or step. In one embodiment, apparatus comprises at least one concentration stage (9) which comprises at least one concentration device and in which the pretreated and steam-treated wood based material (4) or C5 based fraction (7) is concentrated in order to form the concentrated carbohydrate based material (11) and the material stream (10). In one embodiment, apparatus comprises more than one concentration stage (9) which comprises at least one concentration device. In one embodiment, apparatus comprises more than one concentration devices. In one embodiment, apparatus comprises at least one concentration stage (9) which comprises more than one concentration devices. In one embodiment, the concentration stage (9) is an evaporation stage, e.g. a vacuum evaporation, multi-effect evaporation, forced circulation evaporation, film evaporation, or other suitable evaporation or their combinations. In one embodiment, the concentration stage (9) comprises at least one evaporation device. In one embodiment, the evaporation device is selected from the group comprising a vacuum evaporation device, mechanical vapor compressor, thermal vapor compressor, multi-effect evaporation device, forced circulation evaporation device, film evaporator, plate type evaporator, tube evaporator, batch evaporator, continuous evaporator and their combinations.

In this context, a material stream (10) means any material stream which is formed, e.g. by separating, collecting or recovering, from the pretreated and steam-treated wood based material (4) or C5 based fraction (7). The material stream (10) may comprise furfural and also organic acids, such as acetic acid or other organic acids. In one embodiment, the material stream comprises at least water, furfural and organic acids. The material stream may comprise also other components. In one embodiment, the material stream (10) is a fraction of the pretreated and steam-treated wood based material (4) or C5 based fraction (7). In one embodiment, the material stream (10) comprises a fraction of the pretreated and steam-treated wood based material (4) or C5 based fraction (7) and at least a part of steam stream (3). In one embodiment, the material stream (10) may be formed from the pretreated and steam-treated wood based material (4) after any suitable treatment stage. The material stream (10) may be in the form of steam, such as vapor, or liquid, such as condensate.

In this context, the concentrated carbohydrate based material (11) comprises at least C5 carbohydrates. In one embodiment, the concentrated carbohydrate based material (11) comprises C5 and C6 carbohydrates. The concentrated carbohydrate based material (11) may comprise also other agents or components. In one embodiment, the concentrated carbohydrate based material (11) is further concentrated in a post-evaporation stage.

In one embodiment, the material stream (10) is supplied to the recovery stage (12b). In one embodiment, a furfural based fraction (14b) is separated in the recovery stage (12b). In one embodiment, a furfural based fraction (14b) is separated from an aqueous phase (15b).

In one embodiment, the steam stream (3) is supplied to the pretreated and steam-treated wood based material (4) or to the C5 based fraction (7). In one embodiment, the steam stream (3) is supplied to the pretreated and steam-treated wood based material (4) or to the C5 based fraction (7) before or during the concentration stage (9). In one embodiment, volatile components, e.g. furfural and organic acids, are absorbed into the pretreated and steam-treated wood based material (4) or to the C5 based fraction (7). In one embodiment, the pretreated and steam-treated wood based material (4) or to the C5 based fraction (7) is pre-heated by means of the steam stream (3) before the concentration stage (9). Then the energy of the steam stream (3) can be utilized in the heating.

In one embodiment, the steam stream (3) is supplied to the material stream (10). In one embodiment, at least a part of the steam stream (3) is supplied to the material stream (10) after the concentration stage (9).

In one embodiment, the steam stream (3) is supplied to the dilution stage (5).

In one embodiment, the steam stream (3) is cooled or condensed, e.g. by a cooler or condenser, after the steam treatment stage (2), and the cooled steam stream is treated for recovering the furfural based fraction (14a,14b). In one embodiment, the steam stream (3) is cooled or condensed after the steam treatment stage (2), and the cooled steam stream is supplied to the recovery stage (12a,12b) in which the furfural based fraction (14a,14b) is separated. In one embodiment, the steam stream (3) is condensed by water. In one embodiment, the steam stream (3) is supplied to water or aqueous liquid for condensing the steam stream.

In one embodiment, the steam stream (3) is cooled by means at least one heat exchanger (13) after the steam treatment stage (2), and the cooled steam stream is supplied to the recovery stage (12a) in which the furfural based fraction (14a) is separated, and a cooling liquid (16) from the heat exchanger is introduced at least partly to the dilution stage (5).

In one embodiment, the steam stream (3) is purified by means at least one scrubber (17) after the steam treatment stage (2) and is supplied to a recovery stage (12a). In one embodiment, the steam stream (3) is purified by means at least one scrubber (17) after the steam treatment stage (2) and is supplied to the dilution stage (5).

In one embodiment, the steam stream (3) or a part of the steam stream may be recirculated as a recirculation flow (24) back to steam treatment stage (2) for increasing concentration of the steam stream. In one embodiment, pressure of the recirculation flow (24) is increased, e.g. by means of a compressor, before the steam treatment stage (2). In one embodiment, the recirculation flow (24) is supplied to a compressor, e.g. a turbo compressor, and from the compressor to the steam treatment stage (2). The pressure may be increased in one or more steps. In one embodiment, the recirculation flow (24) is used as an additional steam, e.g. as a booster steam, in the steam treatment stage (2), e.g. in the steam explosion. By means of the recirculation of the steam stream furfural concentration may be increased in the steam stream (3).

In one embodiment, the steam stream (3) or a part of the steam stream may be used in a preheating of the pretreated wood based material (1) or in the preheating of the raw material. In one embodiment, the steam stream (3) or a part of the steam stream is supplied to a preheating step of the pretreated wood based material (1). In one embodiment, the steam stream (3) or a part of the steam stream is supplied to a preheating step of the raw material.

In one embodiment, at least a part of C5 based fraction (7) is supplied to the steam stream (3) or to a mixing stage (18) to which the steam stream (3) is supplied, and the steam stream (3) is condensed by the C5 based fraction (7), and the mixture (19) of the steam stream and C5 based fraction is supplied to a recovery stage (12a).

The recovery stage (12a,12b) comprises at least one recovery device. The recovery device may be any suitable recovery device. In one embodiment, the recovery device is a separation device in which the furfural based fraction (14a,14b) is separated from other fractions, e.g. from aqueous phase (15a,15b).

In one embodiment, the recovery stage (12a,12b) comprises at least one separation column and at least one decanter for recovering the furfural based fraction (14a, 14b). In one embodiment, the recovery stage (12a,12b) comprises at least one separation column for recovering the furfural based fraction (14a,14b). In one embodiment, the recovery stage (12a,12b) comprises at least one decanter for recovering the furfural based fraction (14a,14b). In one embodiment, a vapor condensate, e.g. a top vapor condensate, is formed in the separation column. In one embodiment, the vapor condensate is introduced from the separation column to the decanter in which two liquid phases, i.e. furfural based fraction (14a,14b) and aqueous phase (15a, 15b), are separated from each other. In one embodiment, the vapor condensate is supplied out from a suitable part of the separation column, e.g. as a main or side flow. In one embodiment, the vapor condensate is supplied out from a top part of the separation column. In one embodiment, the top vapor condensate is introduced from a top end of the separation column to the decanter in which two liquid phases, i.e. furfural based fraction (14a,14b) and aqueous phase (15a,15b), are separated from each other. Preferably, in the decanter the vapor condensate or the top vapor condensate splits in two liquid phases. In one embodiment, the top vapor condensate is supplied to a bottom part of the decanter. In one embodiment, the furfural based fraction (14a,14b) which comprises at least furfural is recovered in connection with the decanter. In one embodiment, the furfural based fraction (14a,14b) is recovered from an upper part of the decanter and the aqueous phase (15a,15b) is discharged from the bottom part of the decanter. In one embodiment, the separation surface of the furfural based fraction and the aqueous phase is adjusted to a suitable level during the decantation in the decanter. Preferably, the furfural based fraction comprises furfural in high purity, i.e. the furfural based fraction is a furfural rich phase. In one embodiment, by means of the ratio of the furfural based fraction and the aqueous phase and by means of the process conditions can be adjusted the purity of the furfural based fraction. In one embodiment, the aqueous phase (15a,15b) is recirculated to the separation column. The aqueous phase may comprise water and organic acids, such as acetic acid. Further, in one embodiment, the aqueous phase may comprise also furfural. Any suitable device can be used as the recirculating device. In one embodiment, the recirculating device is selected from the group comprising assembly, pump, outlet, inlet, pipe, tube, duct, discharge outlet, discharge valve, discharge channel, conduit, other suitable feeding device, other suitable device and their combinations. In one embodiment, the aqueous phase (15a,15b) is supplied as a reflux to the separation column. Further, in one embodiment, the recovery stage (12a,12b) comprises at least one device for collecting furfural based fraction (14a,14b).

In connection with the separation column a feed, such as material stream (10), steam stream (3), mixture comprising steam stream (19), condensed stream (21), purified stream (22) or cooled steam stream (23), may be introduced to any suitable part of the separation column. In one embodiment, the feed is introduced to the top part of the separation column. In one embodiment, the feed is introduced to the bottom part of the separation column. In one embodiment, the feed is introduced to the middle part of the separation column. In one embodiment, the separation column comprises trays or plates. In one embodiment, the separation column comprises 5-20 stages or trays. In one embodiment, the separation device comprises one or more than one columns. In one embodiment the feed, such as material stream (10), steam stream (3), mixture comprising steam stream (19), condensed stream (21), purified stream (22) or cooled steam stream (23), is introduced to the separation column in counter-current to a vapor formed in the separation column. In one embodiment, the vapor strips out furfural from the feed leading to an increased concentration of furfural at the top part or top end of the separation column. In one embodiment, the aqueous phase (15a,15b) is supplied as the reflux to the separation column in counter-current to the feed.

In one embodiment, the recovery stage (12a,12b) comprises a cooling stage which comprises at least one cooling device and in which the top vapor condensate (6) is cooled before the decanter (10). The cooling device may be any suitable cooling device, e.g. a heat exchanger or condenser.

In one embodiment, the separation column is based on a hetero-azeotropic distillation. In one embodiment, an azeotropic mixture comprises at least furfural and water. In one embodiment, the separation column is a hetero-azeotropic distillation device. In the hetero-azeotropic distillation two liquid phases are on the plate. The top vapor condensate splits in two liquid phases which can be separated in the decanter. In one embodiment, the top vapor condensate comprises at least furfural and water. In one embodiment, the hetero-azeotropic distillation is a batch distillation process. In one embodiment, the hetero-azeotropic distillation is a continuous distillation process.

In one embodiment, a by-product is discharged out from the separation column. In one embodiment, the by-product is discharged from the bottom end of the separation column. The by-product may comprise water, e.g. washing water or dilution water, and/or organic acids, e.g. acetic acid. In one embodiment, the by-product is a water based stream. In one embodiment, the by-product is a residue from the distillation.

In one embodiment, at least one carboxylic acid fraction is recovered in the recovery stage (12a,12b). In one embodiment, an acetic acid fraction is recovered in the recovery stage (12a,12b). The carboxylic acid fraction may be recovered from the bottom of the separation column or from any suitable part, such as from a desired tray or plate, of the separation column.

In one embodiment, the furfural based fraction (14a,14b) is purified and/or concentrated in at least one furfural purification stage comprising at least one purification device after the decanter. In one embodiment, the purification device may be an additional distillation device or the second separation column, e.g. hetero-azeotropic distillation device, or other suitable device.

In one embodiment, the furfural based fraction (14a,14b) comprises furfural over 70% by weight, preferably over 80% by weight, more preferably over 90% by weight and most preferably over 95% by weight.

In one embodiment, the method is based on a continuous process. In one embodiment, the apparatus is a continuous apparatus. In one embodiment, the method is based on a batch process. In one embodiment, at least a part of the apparatus is a batch apparatus.

A furfural based product comprising the furfural based fraction (14a,14b) may be formed according to any method or apparatus defined above. In one embodiment, the furfural based product is in the form of liquid.

A chemical product comprising a carboxylic acid fraction may be formed according to any method or apparatus defined above. In one embodiment, the chemical product is in the form of liquid.

The furfural based fraction (14a,14b) may be used as a source material in an additional treatment, chemical treatment, polymerization process, manufacture of a chemical, plastic, cellulose acetate or varnish, or other suitable process, or as a component in a fuel or combustion material, or their combinations.

The method and the apparatus provide furfural and also carbohydrate streams with good quality. By means of the method and apparatus carbohydrate based streams can be purified and waste water treatment plant loading, and also chemical oxygen demand (COD), can be reduced and valuable components can be recovered. Further, by means of the method and apparatus energy recirculation can be improved.

The method and the apparatus provide an industrially applicable, simple and affordable way of separating and recovering furfural. The method or the apparatus is easy and simple to realize as a production process. The method and the apparatus are suitable for use in connection with the manufacture of the different lignin and carbohydrate products from different raw materials.

EXAMPLES

Some embodiments of the invention are described in more detail by the following examples with reference to accompanying drawings.

Example 1

Figure 2:
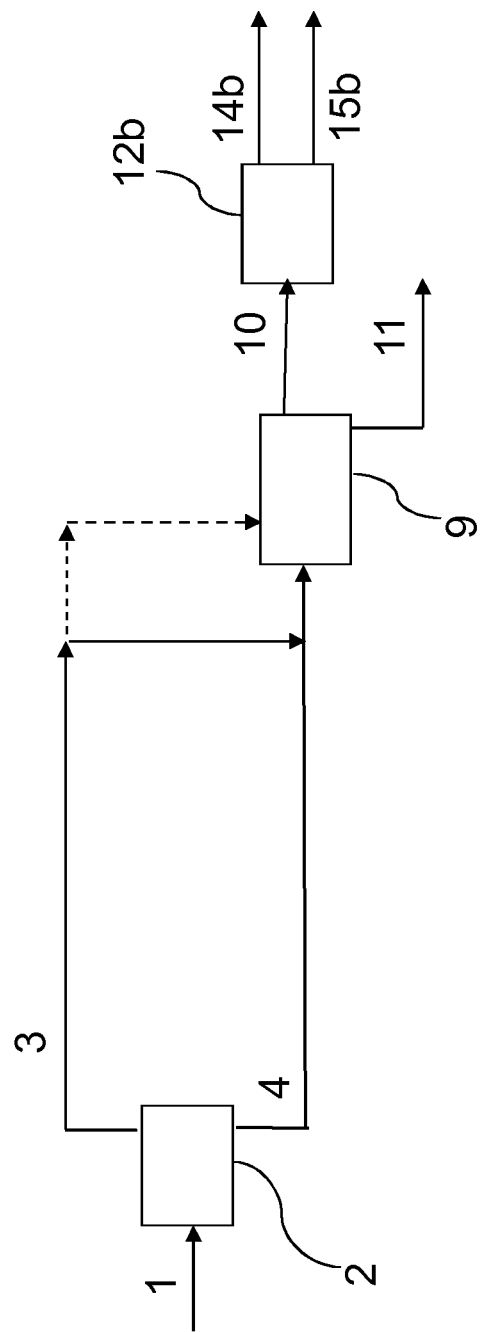
FIG. 2 is a flow chart illustration of a method according to another embodiment.

In this example, furfural is recovered from a steam stream (3) according to a process of FIG. 1 and FIG. 2.

The steam stream (3) is formed in a treatment of a pretreated wood based material (1). The pretreated wood based material (1) which comprises at least carbohydrates is treated in a steam treatment stage (2), such as in a steam explosion stage, which comprises at least one steam treatment device, e.g. steam explosion device, and in which the steam is released. The steam stream (3) and pretreated and steam-treated wood based material (4) are separated in connection with the steam treatment stage (2), for example by means of at least one separation device, e.g. cyclone. The steam stream (3) which comprises furfural is supplied out from the steam treatment stage (2) by means of at least one discharge means. Also the pretreated and steam-treated wood based material (4) which comprises carbohydrates is supplied out from the steam treatment stage (2) by means of at least one discharge means. The pretreated wood based material has been formed from raw material by pretreating the raw material. The raw material is wood based material or a mixture comprising wood based material. The steam stream (3) is in the form of steam, such as water based steam.

According to FIG. 1, the pretreated and steam-treated wood based material (4) is diluted in a dilution stage (5) and is treated in a separation stage (6) in which C5 based fraction (7) and C6 based fraction (8) are separated. C5 based fraction (7) is supplied to a concentration stage (9) comprising at least one concentration device, e.g. an evaporation device, in which the C5 based fraction is concentrated in order to form a concentrated carbohydrate based material (11) and the material stream (10) which comprises furfural. The steam stream (3) is supplied into the C5 based fraction (7) before or during the concentration stage (9). Alternatively, according to FIG. 2, the pretreated and steam-treated wood based material (4) is supplied directly from the steam treatment stage (2) to the concentration stage (9) and the steam stream (3) is supplied into the pretreated and steam-treated wood based material before or during the concentration stage (9). In the process according to FIG. 1 or 2, the material stream (10) is collected during the concentration. The material stream may be a vapor or a condensate of vapor from the concentration device.

The material stream (10) is treated in at least one recovery stage (12b) for recovering a furfural based fraction (14b). The material stream (10) is supplied to the recovery stage (12b) in which the furfural based fraction (14b) is separated from an aqueous phase (15b).

In this example, the recovery stage (12b) comprises at least one separation column which is based on a hetero-azeotropic distillation and in which at least a top vapor condensate comprising at least furfural and water is formed, and at least one decanter to which the top vapor condensate is introduced from a top end of the separation column and in which two liquid phases (14b,15b) are separated from each other. Further, the recovery stage may comprise a cooling device in which the top vapor condensate may be cooled before the decanter. Further, the recovery stage comprises at least one recirculating device for supplying an aqueous phase (15b) as a reflux from the decanter to the separation column. Carboxylic acid fraction or fractions may be recovered in the separation column. Further, by-products may be discharged out from the separation column. The by-product may comprise water and/or organic acids, e.g. acetic acid. Preferably, the material stream (10) is introduced to the separation column in counter-current to a vapor formed in the separation column. Preferably, the aqueous phase (15b) is supplied as the reflux to the separation column in counter-current to the material stream (10).

Further, the furfural based fraction (14b) may be purified and/or concentrated in at least one furfural purification stage comprising at least one purification device after the decanter.

Example 2

Figure 3:
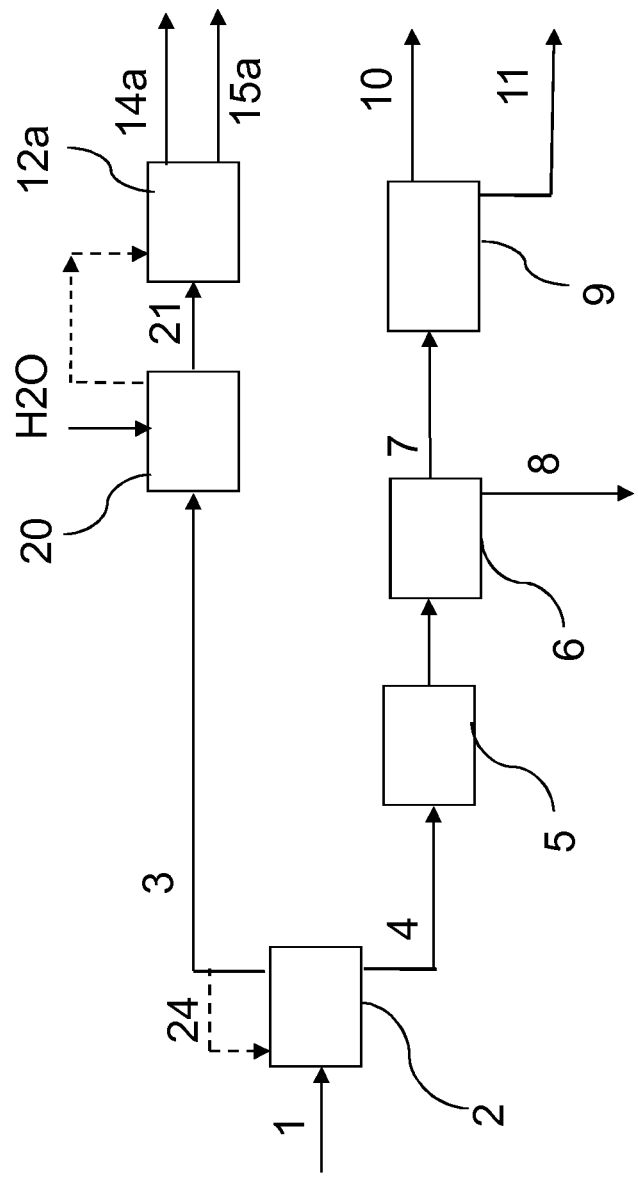
FIG. 3 is a flow chart illustration of a method according to another embodiment.

In this example, furfural is recovered from a steam stream (3) according to a process of FIG. 3.

The steam stream (3) is formed in a treatment of a pretreated wood based material (1). The pretreated wood based material (1) which comprises at least carbohydrates is treated in a steam treatment stage (2), such as in a steam explosion stage, which comprises at least one steam treatment device, e.g. steam explosion device, and in which the steam is released. The steam stream (3) and pretreated and steam-treated wood based material (4) are separated in connection with the steam treatment stage (2), for example by means of at least one separation device, e.g. cyclone. The steam stream (3) which comprises furfural is supplied out from the steam treatment stage (2) by means of at least one discharge means. Also the pretreated and steam-treated wood based material (4) which comprises carbohydrates is supplied out from the steam treatment stage (2) by means of at least one discharge means. The pretreated wood based material has been formed from raw material by pretreating the raw material. The raw material is wood based material or a mixture comprising wood based material. The steam stream (3) is in the form of steam.

The pretreated and steam-treated wood based material (4) can be diluted in a dilution stage (5) and can be treated in a separation stage (6) in which C5 based fraction (7) and C6 based fraction (8) are separated. C5 based fraction (7) is supplied to a concentration stage (9) comprising at least one concentration device, e.g. an evaporation device, in which the C5 based fraction is concentrated in order to form a concentrated carbohydrate based material (11) and the material stream (10) which comprises furfural.

The steam stream (3) is supplied to a condensing stage (20) in which the steam stream (3) is condensed with water. The steam stream or a part of the steam stream (24) may be recirculated back to steam treatment stage (2) for increasing concentration of the steam stream. This recirculation may be carried out also in the processes of the other examples.

The condensed stream (21) is supplied to the recovery stage (12a) in which the furfural based fraction (14a) is separated from an aqueous phase (15a). Further, a vapor flow from the condensing stage (20) may be introduced to the recovery stage (12a).

In this example, the recovery stage (12a) comprises at least one separation column which is based on a hetero-azeotropic distillation and in which at least a top vapor condensate comprising at least furfural and water is formed, and at least one decanter to which the top vapor condensate is introduced from a top end of the separation column and in which two liquid phases (14a,15a) are separated from each other. Further, the recovery stage may comprise a cooling device in which the top vapor condensate may be cooled before the decanter. Further, the recovery stage comprises at least one recirculating device for supplying an aqueous phase (15a) as a reflux from the decanter to the separation column. Carboxylic acid fraction or fractions may be recovered in the separation column. Further, by-products may be discharged out from the separation column. The by-product may comprise water and/or organic acids, e.g. acetic acid. Preferably, the condensed stream (21) is introduced to the separation column in counter-current to a vapor formed in the separation column. Preferably, the aqueous phase (15a) is supplied as the reflux to the separation column in counter-current to the condensed stream (21).

Further, the furfural based fraction (14a) may be purified and/or concentrated in at least one furfural purification stage comprising at least one purification device after the decanter.

Example 3

Figure 4:
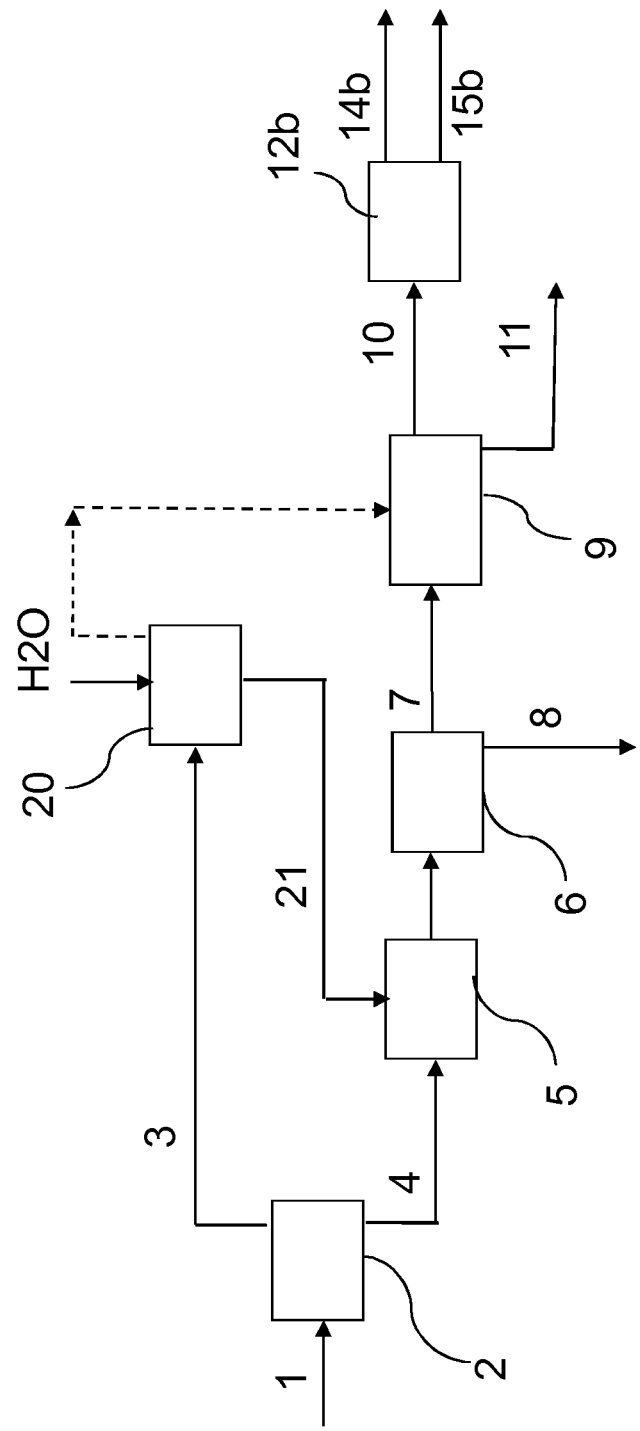
FIG. 4 is a flow chart illustration of a method according to another embodiment.

In this example, furfural is recovered from a steam stream (3) according to a process of FIG. 4.

The steam stream (3) is formed in a treatment of a pretreated wood based material (1). The pretreated wood based material (1) which comprises at least carbohydrates is treated in a steam treatment stage (2), such as in a steam explosion stage, which comprises at least one steam treatment device, e.g. steam explosion device, and in which the steam is released. The steam stream (3) and pretreated and steam-treated wood based material (4) are separated in connection with the steam treatment stage (2), for example by means of at least one separation device, e.g. cyclone. The steam stream (3) which comprises furfural is supplied out from the steam treatment stage (2) by means of at least one discharge means. Also the pretreated and steam-treated wood based material (4) which comprises carbohydrates is supplied out from the steam treatment stage (2) by means of at least one discharge means. The pretreated wood based material has been formed from raw material by pretreating the raw material. The raw material is wood based material or a mixture comprising wood based material. The steam stream (3) is in the form of steam, such as water based steam.

The pretreated and steam-treated wood based material (4) is diluted in a dilution stage (5) and is treated in a separation stage (6) in which C5 based fraction (7) and C6 based fraction (8) are separated. C5 based fraction (7) is supplied to a concentration stage (9) comprising at least one concentration device, e.g. an evaporation device, in which the C5 based fraction is concentrated in order to form a concentrated carbohydrate based material (11) and the material stream (10) which comprises furfural.

The steam stream (3) is supplied to a condensing stage (20) in which the steam stream (3) is condensed with water. The condensed stream (21) is supplied to the dilution stage (5) in which the condensed stream is used as a dilution liquid. Further, a vapor flow from the condensing stage (20) may be introduced to the concentration stage (9).

The material stream (10) is collected during the concentration. The material stream may be a vapor or a condensate of vapor from the concentration device. The material stream (10) is treated in at least one recovery stage (12b) for recovering a furfural based fraction (14b). The material stream (10) is supplied to the recovery stage (12b) in which the furfural based fraction (14b) is separated from an aqueous phase (15b).

In this example, the recovery stage (12b) comprises at least one separation column which is based on a hetero-azeotropic distillation and in which at least a top vapor condensate comprising at least furfural and water is formed, and at least one decanter to which the top vapor condensate is introduced from a top end of the separation column and in which two liquid phases (14b,15b) are separated from each other. Further, the recovery stage may comprise a cooling device in which the top vapor condensate may be cooled before the decanter. Further, the recovery stage comprises at least one recirculating device for supplying an aqueous phase (15b) as a reflux from the decanter to the separation column. Carboxylic acid fraction or fractions may be recovered in the separation column. Further, by-products may be discharged out from the separation column. The by-product may comprise water and/or organic acids, e.g. acetic acid. Preferably, the material stream (10) is introduced to the separation column in counter-current to a vapor formed in the separation column. Preferably, the aqueous phase (15b) is supplied as the reflux to the separation column in counter-current to the material stream (10).

Further, the furfural based fraction (14b) may be purified and/or concentrated in at least one furfural purification stage comprising at least one purification device after the decanter.

Example 4

Figure 5:
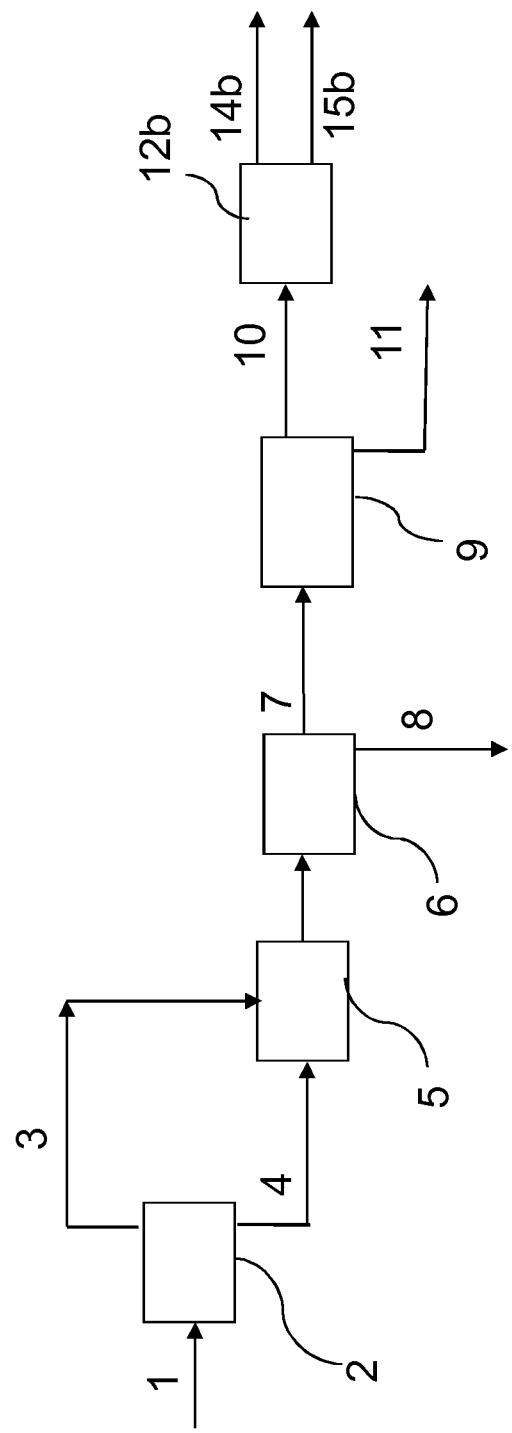
FIG. 5 is a flow chart illustration of a method according to another embodiment.

In this example, furfural is recovered from a steam stream (3) according to a process of FIG. 5.

The pretreated wood based material (1) and the pretreated and steam-treated wood based material (4) are treated according to Example 1 and FIG. 1. The steam stream (3) is supplied to the dilution stage (5). A mixture of the pretreated and steam-treated wood based material (4) and the steam stream (3) is treated according to Example 1 and FIG. 1 for recovering a furfural based fraction (14b).

Example 5

Figure 6:
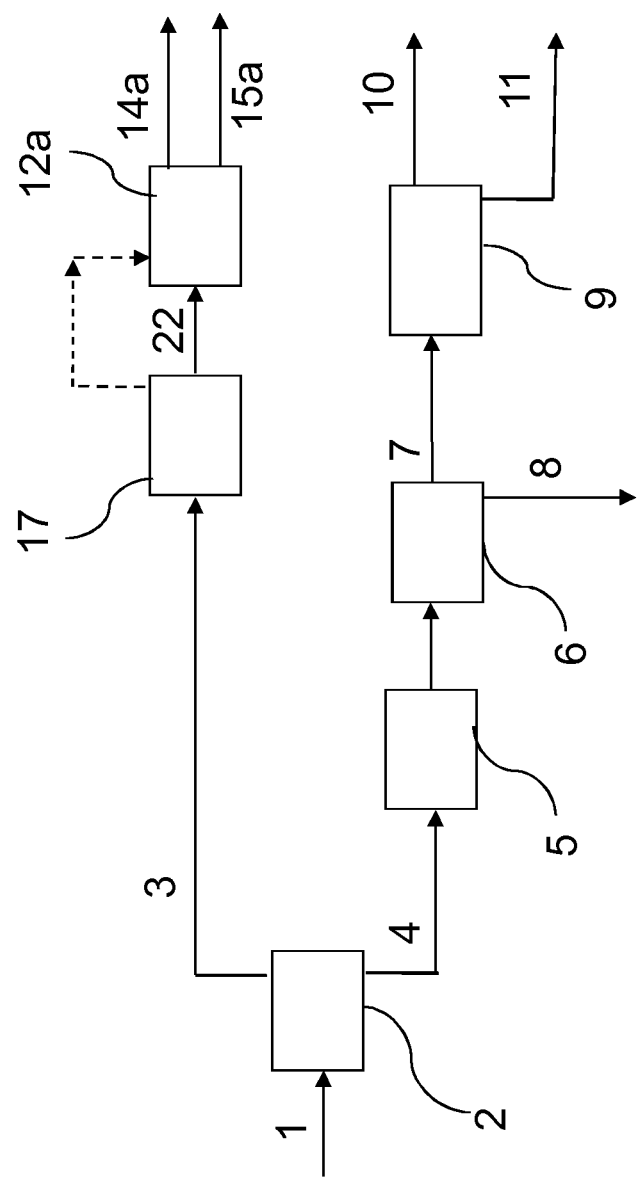
FIG. 6 is a flow chart illustration of a method according to another embodiment.

In this example, furfural is recovered from a steam stream (3) according to a process of FIG. 6.

The pretreated wood based material (1) and the pretreated and steam-treated wood based material (4) are treated according to Example 2 and FIG. 3. The steam stream (3) is purified by means at least one scrubber (17) after the steam treatment stage (2), and a purified stream (22) is supplied to a recovery stage (12a). The purified stream (22) is treated in the recovery stage (12a) according to Example 2 for recovering a furfural based fraction (14a). Further, a vapor flow from the scrubber (17) may be introduced to the recovery stage (12a).

Example 6

Figure 7:
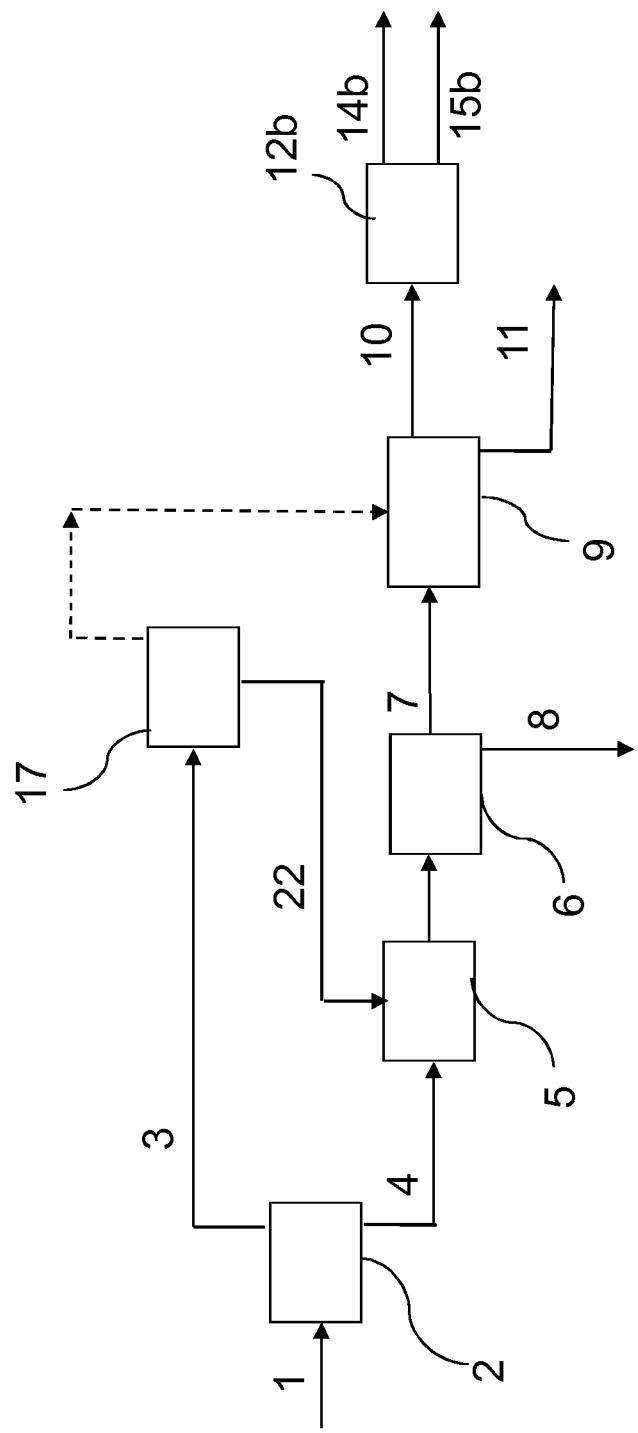
FIG. 7 is a flow chart illustration of a method according to another embodiment.

In this example, furfural is recovered from a steam stream (3) according to a process of FIG. 7.

The pretreated wood based material (1) and the pretreated and steam-treated wood based material (4) are treated according to Example 3 and FIG. 4. The steam stream (3) is purified by means at least one scrubber (17) after the steam treatment stage (2), and a purified stream (22) is supplied to a dilution stage (5) in which the purified stream is used as a dilution liquid. Further, a vapor flow from the scrubber (17) may be introduced to the concentration stage (9). A mixture of the pretreated and steam-treated wood based material (4) and the purified stream (22) is treated according to Example 3 and FIG. 4 for recovering a furfural based fraction (14b).

Example 7

Figure 8:
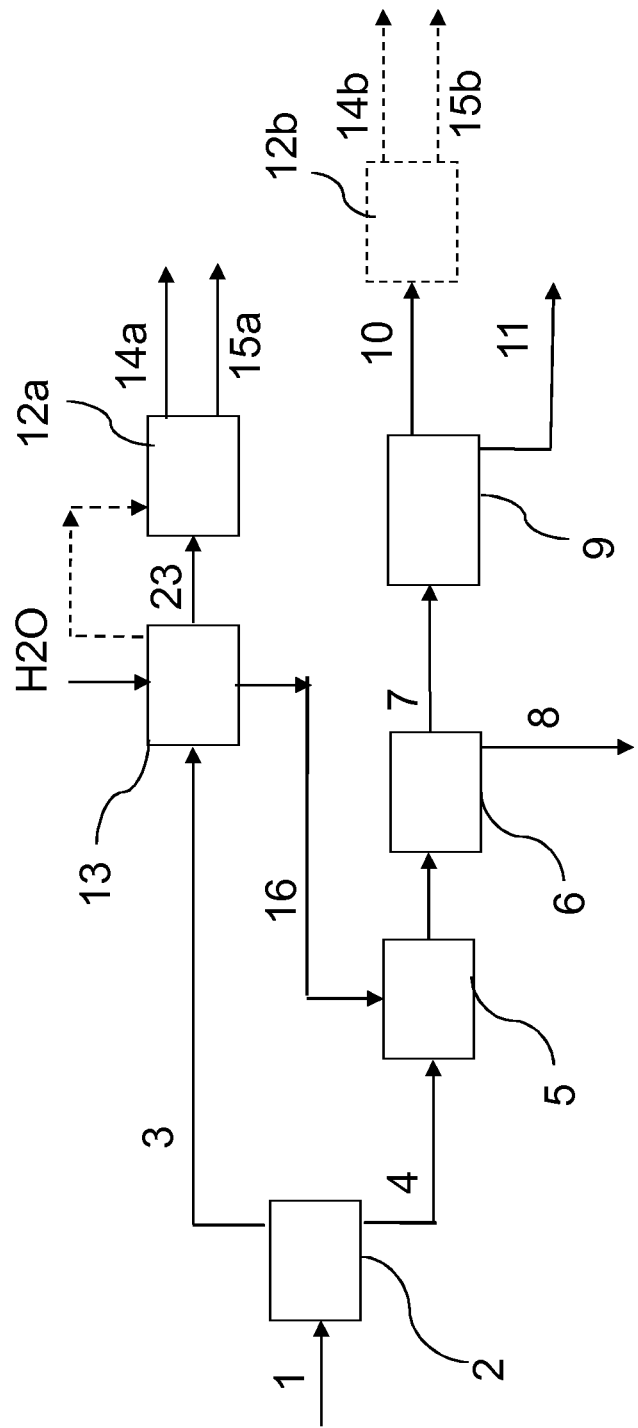
FIG. 8 is a flow chart illustration of a method according to another embodiment.

In this example, furfural is recovered from a steam stream (3) according to a process of FIG. 8.

The pretreated wood based material (1) and the pretreated and steam-treated wood based material (4) are treated according to Example 2 and FIG. 3. The steam stream (3) is cooled by means at least one heat exchanger (13) after the steam treatment stage (2). The cooling is made by water in the heat exchanger. The cooled steam stream (23) is supplied to a recovery stage (12a). The cooled steam stream (23) is treated in the recovery stage (12a) according to Example 2 for recovering a furfural based fraction (14a). Further, a vapor flow from the heat exchanger (13) may be introduced to the recovery stage (12a).

A cooling water (16) from the heat exchanger is introduced at least partly to the dilution stage (5) in which the cooling water (16) is used as a dilution liquid. Further, a material stream (10) may be treated in a recovery stage (12b) according to Example 1 for recovering a furfural based fraction (14b).

Example 8

Figure 9:
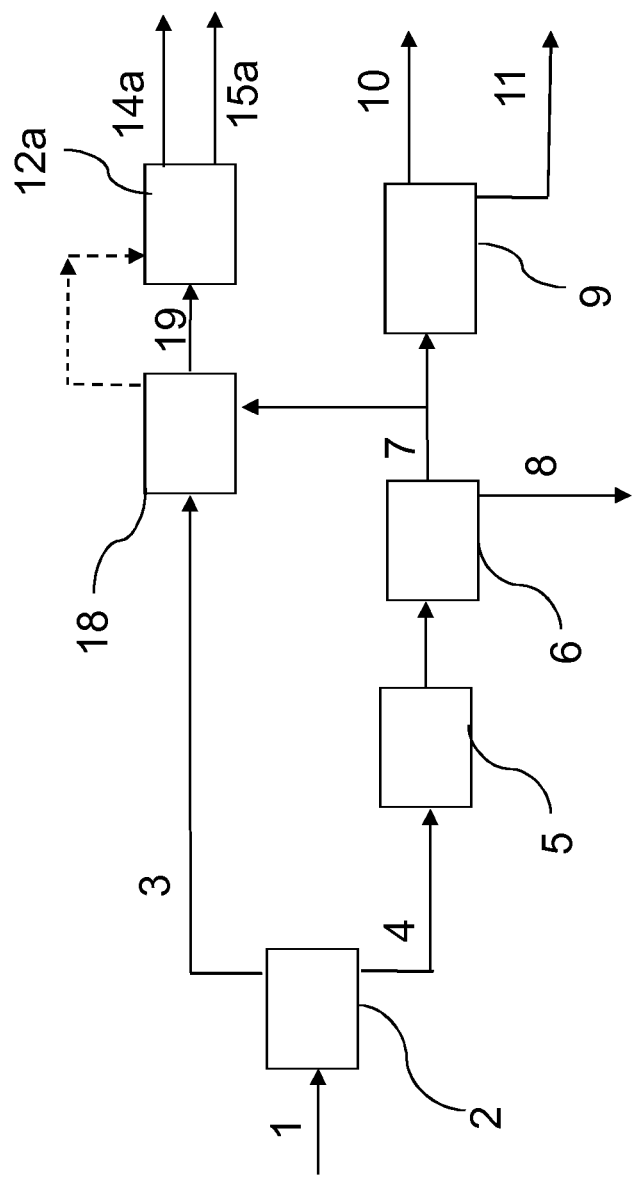
FIG. 9 is a flow chart illustration of a method according to another embodiment.

In this example, furfural is recovered from a steam stream (3) according to a process of FIG. 9.

The pretreated wood based material (1) and the pretreated and steam-treated wood based material (4) are treated according to Example 2 and FIG. 3. At least a part of C5 based fraction (7) is supplied to a mixing stage (18). Also the steam stream (3) from the steam treatment stage (2) is supplied to the mixing stage (18) in which the steam stream and C5 based fraction is mixed. Alternatively, a part of C5 based fraction (7) can be fed directly to the steam stream (3). The steam stream (3) is condensed by the C5 based fraction (7). The mixture (19) of the steam stream and C5 based fraction is supplied to a recovery stage (12a). The mixture (19) is treated in the recovery stage (12a) according to Example 2 for recovering a furfural based fraction (14a). Further, a vapor flow from the mixing stage (18) may be introduced to the recovery stage (12a).

Example 9

In this example material streams (10) of a multistage concentration was studied.

A diluted acid pretreated birch based material (1) was treated by means of a steam treatment stage (2) comprising a steam explosion according to the process of FIG. 1. A pretreated and steam-treated wood based material (4) was diluted in a dilution stage (5) and was treated in a separation stage (6) in which C5 based fraction (7) and C6 based fraction (8) were separated. C5 based fraction (7) was supplied to a concentration stage (9) which comprises two steps. The evaporation was performed by means of a laboratory scale rotary evaporator in vacuum conditions and at temperature of about 78° C. Samples were collected from vapor and carbohydrate streams of the concentration after each steps of the concentration stage.

The C5 based fraction (7) contained carbohydrates, e.g. xylose and glucose, 59 g/l and furfural 4.45 g/l. A concentrated carbohydrate based flow of sample 1 after the first step contained carbohydrates 100 g/l and furfural 0.58 g/l. $1^{st}$ condensate of sample 1 after the first step contained carbohydrates 0 g/l and furfural 10 g/l. A concentrated carbohydrate based flow of sample 2 after the second step contained carbohydrates 363 g/l and furfural 0.04 g/l. $2^{nd}$ condensate of sample 2 after the second step contained carbohydrates 0 g/l and furfural 0.49 g/l. The carbohydrate and furfural contents of the C5 based fraction (7), concentrated carbohydrate based materials (11) and $1^{st}$ and $2^{nd}$ condensates are shown in table 1.

TABLE 1

|  | C5 based fraction | Carbohydrate based flow of sample 1 | $1^{st}$ condensate of sample 1 | Carbohydrate based flow of sample 2 | $2^{nd}$ condensate of sample 2 |
| --- | --- | --- | --- | --- | --- |
| Carbohydrates, g/l | 59 | 100 | 0 | 363 | 0 |
| Furfural, g/l | 4.45 | 0.58 | 10 | 0.04 | 0.49 |

It was observed that furfural accumulated mainly into the vapor stream, i.e. 1 st condensate, during the first step of the concentration stage, and therefore the material stream (10) comprising furfural was mainly collected during the first concentration step.

The method and apparatus according to the present invention is suitable in different embodiments to be used in different furfural recovery processes. Further, the method and apparatus according to the present invention is suitable in different embodiments to be used for producing the most different kinds of carbohydrate fractions and chemical products from different raw materials.

The invention is not limited merely to the example referred to above; instead many variations are possible within the scope of the inventive idea defined by the claims.

The invention claimed is:

1. A method for recovering furfural from a steam stream formed in a treatment of a pretreated wood based material, the method comprising:
   treating the pretreated wood based material, which comprises carbohydrates, in a steam treatment stage in which the steam stream is released;
   supplying the steam stream, which comprises furfural, out from the steam treatment stage;

supplying a pretreated and steam-treated wood based material, which comprises carbohydrates, out from the steam treatment stage;

combining the steam stream with at least one of (a) the pretreated and steam-treated wood based materials, (b) a C5 based fraction separated from the pretreated and steam-treated wood based material, or (e) a material stream formed from the C5 based fraction or the pretreated and steam-treated wood based ma al to form a forme stream; and treating the formed stream in a recovery stage for recovering a furfural based fraction.

2. The method according to claim 1, wherein the steam treatment stage is a steam explosion stage.

3. The method according to claim 1, further comprising:
cooling the steam stream after the steam treatment stage and;
treating the cooled steam stream for recovering the furfural based fraction.

4. The method according to claim 1, further comprising:
diluting the pretreated and steam-treated wood based material in a dilution stage; and
treating the pretreated and steam-treated wood based material in a separation stage in which a C5 based fraction and a C6 based fraction are separated.

5. The method according to claim 4, further comprising supplying the pretreated and steam-treated wood based material or the C5 based fraction to a concentration stage for forming a concentrated carbohydrate based material and a material stream, which comprises furfural.

6. The method according to claim 1, further comprising supplying a material stream to the recovery stage.

7. The method according to claim 1, further comprising:
cooling the steam stream after the steam treatment stage; and
supplying the cooled steam stream to the recovery stage in which the furfural based fraction is separated.

8. The method according to claim 1, further comprising condensing the steam stream by water.

9. The method according to claim 6, further comprising supplying the steam stream to the material stream.

10. The method according to claim 4, further comprising supplying the steam stream to the dilution stage.

11. The method according to claim 4, further comprising supplying the steam stream to the pretreated and steam-treated wood based material or to the C5 based fraction.

12. The method according to claim 1, further comprising:
purifying the steam stream using at least one scrubber after the steam treatment stage and;
supplying the steam stream to the recovery stage.

13. The method according to claim 4, further comprising:
purifying the steam stream using at least one scrubber after the steam treatment stage; and
supplying the steam stream to the dilution stage.

14. The method according to claim 4, further comprising:
cooling the steam stream using at least one heat exchanger after the steam treatment stage;
supplying the cooled steam stream to the recovery stage in which the furfural based fraction is separated; and
introducing a cooling liquid from the heat exchanger at least partly to the dilution stage.

15. The method according to claim 1, further comprising recirculating the steam stream or a part of the steam stream as a recirculation flow back to the steam treatment stage for increasing concentration of the steam stream.

16. The method according to claim 4, further comprising:
supplying at least a part of the C5 based fraction to the steam stream or to a mixing stage to which the steam stream is supplied;
condensing the steam stream by the C5 based fraction; and
supplying the mixture of the steam stream and the C5 based fraction to the recovery stage.

17. The method according to claim 1, wherein the recovery stage comprises at least one separation column and at least one decanter for recovering the furfural based fraction.

18. The method according to claim 1, wherein the recovery stage comprises at least one decanter for recovering the furfural based fraction.

19. The method according to claim 1, wherein the recovery stage comprises at least one separation column for recovering the furfural based fraction.

20. The method according to claim 1, further comprising forming the pretreated wood based material from raw material, which is a wood based material or a mixture comprising wood based material.

21. An apparatus for recovering furfural from a steam stream, which is formed in a treatment of a pretreated wood based material, the apparatus comprising:
at least one a steam treatment stage in which the pretreated wood based material, which comprises at least carbohydrates, is treated and in which the steam is released;
at least one discharge means for supplying the steam stream, which comprises furfural, out from the steam treatment stage;
at least one discharge means for supplying a pretreated and steam-treated wood based material, which comprises carbohydrates, out from the steam treatment stage;
at least one combining means for combining the steam stream with at least one of (a) the pretreated and steam-treated wood based material, (b) a C5 based fraction separated from the pretreated and steam-treated wood based material, or (c) a material stream formed from the C5 based fraction or the pretreated and steam-treated wood based material to form a formed steam stream; and
at least one recovery stage for recovering a furfural based fraction-from the formed steam stream.

* * * * *

UNITED STATES PATENT AND TRADEMARK OFFICE
CERTIFICATE OF CORRECTION

PATENT NO. : 11,040,950 B2  Page 1 of 1
APPLICATION NO. : 16/473790
DATED : June 22, 2021
INVENTOR(S) : Juha Tamper et al.

It is certified that error appears in the above-identified patent and that said Letters Patent is hereby corrected as shown below:

In the Claims

At Column 15, Line 7 (Claim 1, Line 15), please delete "or (e) a material" and insert --or (c) a material-- therefor.

At Column 15, Lines 9-10 (Claim 1, Lines 17-18), please delete "steam-treated wood based ma al to form a forme stream; and" and insert --steam-treated wood based material to form a formed stream; and-- therefor.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*